United States Patent [19]
Lucas

[11] Patent Number: 5,207,988
[45] Date of Patent: May 4, 1993

[54] APPARATUS FOR DETECTING AND QUANTIFYING CLOT LYSIS AND ESTABLISHING OPTIMUM MEDICATION AND DOSAGES

[75] Inventor: Frederick V. Lucas, Fort Lauderdale, Fla.

[73] Assignee: The Cleveland Clinic Foundation, Cleveland, Ohio

[21] Appl. No.: 376,246

[22] Filed: Jul. 6, 1989

[51] Int. Cl.$^5$ ............................................. G01N 11/04
[52] U.S. Cl. .................................. 422/73; 422/81; 422/82.05; 435/287; 435/810
[58] Field of Search .................... 422/73, 81, 58, 82, 422/55; 435/13, 810, 287; 436/63, 178

[56] References Cited

U.S. PATENT DOCUMENTS 4,756,884 7/1988 Hillman et al. ............... 422/73
4,770,779 9/1988 Ichikawa et al. ............. 436/178

Primary Examiner—James C. Housel
Assistant Examiner—Daniel Redding
Attorney, Agent, or Firm—Fay, Sharpe, Beall, Fagan, Minnich & McKee

[57] ABSTRACT

A method and apparatus for detecting clot lysis, comprising allowing a blood sample containing a plasminogen activator to traverse a capillary track, wherein the capillary track contains a reagent capable of initiating blood clotting and the sample contacts the reagent as the sample flows through the track, the capillary track being of sufficient length and sufficiently small volume to allow blood to clot in the track before the sample reaches the end of the track and while a reserve sample volume remains available for continued capillary flow; allowing the sample to clot in the capillary track; and measuring time required for the sample to resume flowing as a measure of clot lysis.

8 Claims, 1 Drawing Sheet

APPARATUS FOR DETECTING AND QUANTIFYING CLOT LYSIS AND ESTABLISHING OPTIMUM MEDICATION AND DOSAGES

INTRODUCTION

1. Technical Field

This invention is directed to methods for detecting and quantifying clot lysis, particularly as a result of treatment of clots with thromboembolytic agents.

2. Background

Thromboembolytic therapy is being increasingly used to treat patients with occlusive coronary, peripheral, and cerebrovascular diseases. A number of factors are known to influence the success of therapy, including the dosing regimen used, the timing therapy in relationship to the age of thrombus, the size of the thrombus, and the site of infusion (intraclot vs. intravenous). A number of questions relating to therapy remain, including determination of the most effective thrombolytic agent, optimization of dose and method of administration, and prevention of unwanted side effects. The most prominent side effects include re-thrombosis following cessation of therapy and hemorrhage during the immediately after therapy.

Thromboembolytic therapy differs from anticoagulant therapy in that its thrust is to re-establish vascular patency by clot dissolution, whereas the goal of anticoagulant treatment is to prevent further propagation of a thrombus. Thrombolysis is achieved by activation of the fibrinolytic system. The central feature of this system is conversion of the zymogen plasminogen to the enzyme plasmin which then proteolytically degrades a number of substrates including fibrinogen, fibrin, Factor V, Factor VIII, and platelet membrane glycoprotein Ib. In theory, activation of plasminogen within a clot yields clot-specific lysis, whereas activation of plasminogen in the circulating blood yields a combination of fibrin degradation within the clot and degradation of circulating fibrinogen. The latter has been termed the "systemic lytic state." Significant disagreement exists as to the contribution of the systemic lytic state to the safety and efficacy of different thrombolytic agents.

Monitoring thrombolytic therapy using laboratory tests is based on the concept that an in vitro test using circulating venous blood can predict the efficacy and safety of thrombolytic agents. Laboratory monitoring is currently controversial both because (1) currently available test do not provide an adequate global overview of the fibrinolytic system using a test that is rapid, reproducible, and sensitive to changes in individual components of the fibrinolytic system, and (2) uncertainty caused by lack of suitable testing has led some to question whether monitoring of circulating venous blood can adequately be used to predict in vivo effects. The situation is very different from that in the coagulation cascade in which, for example, the prothrombin time assay provides a relatively sensitive and useful indication of changes in the extrinsic pathway during anticoagulant therapy.

There are four types of laboratory test that are being employed to monitor fibrinolysis: (1) global tests of the pathway; (2) measurement of specific components in the pathway; (3) measuring markers of lytic activity; and (4) tests to predict recurrent thrombosis following lytic therapy. In general, the available global tests are simple to use but lack sensitivity and reproducibility. Additionally, the turnaround time for these tests is such that the data provided is too late to be clinically useful. Tests of individual components of the fibrinolytic system are becoming increasingly available and are better standardized. These tests provide, in general, excellent reproducibility and sensitivity, but they do not provide results with acceptable turnaround times. Worse, they do not provide a clinically useful overall view of the status of the hemostatic mechanism, much less the status of the fibrinolytic system.

A definition of the systemic lytic state has not been altogether standardized. However, most investigators consider the state to exist if the concentration of fibrinogen in plasma is less than 1 mg/ml. The most common technique employed for measuring fibrinogen in clinical investigations of thrombolytic therapy has been a modification of the Clauss technique. The suitability of this technique has been somewhat uncertain, since it does not give a detailed reflection of the chemical state of this protein (native fibrinogen vs. breakdown fragments vs. high molecular weight polymers) and since the presence of fibrin and fibrinogen degradation products may spuriously lower the apparent value. Nevertheless, measurement of fibrinogen or the thrombin time is the method of choice for most clinical studies because of its relative simplicity and rapid turnaround time.

Plasminogen activators currently used in clinical practice for thrombolytic therapy include urokinase, streptokinase, and tissue plasminogen activator (TPA). There are several indications and levels of FDA approval for these agents, but in general, the available agents provide enough comparability in clinical results that there is significant controversy regarding the relative superiority of one over another. Differing therapeutic regimens exist for different investigators and clinicians, but the therapeutic doses typically are not tailored to individual patients. The standard approach taken is to administer a plasminogen activator, determine that a systemic lytic state does or does not exist, and monitor the clinical results by imaging or other physical techniques. Extensive and sophisticated laboratory studies of biochemical changes induced in the hemostatic mechanism have been made, but these data are not generally produced in the course of routine patient care, nor are they especially useful in guiding the therapy. It would be desirable to tailor treatment to fit the individual patient, but this requires improved methods for detecting and quantifying clot lysis.

Accordingly, there remains a need for improved methods of detecting and quantifying clot lysis and evaluating reagents and dosages for the individual patient using simple, sensitive, reproducible technology with a rapid turnaround time and a proven relevance to in vitro activity.

SUMMARY OF THE INVENTION

The present invention provides a method for detecting and evaluating clot lysis, potential dosage and effectiveness of thromboembolytic agents on an individual patient by patient basis.

In one aspect, the method comprises the steps of allowing a blood sample containing a plasminogen activator to traverse a capillary track, wherein the capillary track contains a reagent capable of initiating blood clotting and the sample contacts the reagent as the sample flows through the track, the capillary track being of sufficient length and sufficiently small volume to allow blood to clot in the track before the sample reaches the end of the track and while a reserve sample volume remains available for continued capillary flow, allowing the sample to clot in the capillary track, and measuring time required for the sample to resume flowing as a measure of clot lysis.

In another aspect, the present invention provides a method which comprises the steps of allowing a blood sample substantially free of plasminogen activator to traverse, a capillary track, wherein the capillary track contains a reagent capable of initiating blood clotting and the sample contacts the reagent as the sample flows through the track, the capillary track being of sufficient length and sufficiently small volume to allow blood to clot in the track before the sample reaches the end of the track and while a reserve sample volume remains available for continued capillary flow, allowing the sample to clot in the capillary track, allowing a second sample of blood from the same patient, to traverse a second capillary track into contact with said clot, said second blood sample containing a plasminogen activator, said clot being such that at least some flow of said second blood sample is possible either through and/or around said clot and measuring the time required for the first sample to resume full flowing as a measure of clot lysis.

Still another aspect of the present invention involves a method of developing data to facilitate selection of the most efficacious plasminogen activator for a particular individual patient comprising the steps of allowing a blood sample containing a first plasminogen activator to traverse a capillary track, wherein the capillary track contains a reagent capable of initiating blood clotting and the sample contacts the reagent as the sample flows through the track, the capillary track being of sufficient length and sufficiently small volume to allow blood to clot in the track before the sample reaches the end of the track and while a reserve sample volume remains available for continued capillary flow, allowing the sample to clot in the capillary track, and measuring time required for the sample to resume flowing as a measure of clot lysis;

repeating the foregoing steps using higher and lower dosages of plasminogen activation;

further repeating said steps substituting at least one further plasminogen activator.

Yet another aspect of the present invention involves a novel apparatus for carrying out one of the preferred methods of the present invention.

DESCRIPTION OF THE DRAWINGS

FIGS. 2a shows an alternative embodiment of the device of FIG. 2.

DESCRIPTION OF SPECIFIC EMBODIMENTS

Figure 1A:
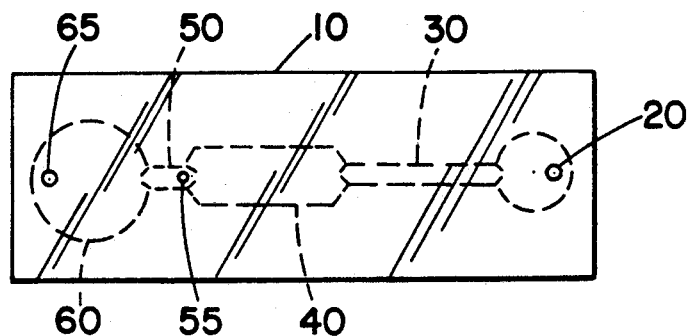
FIGS. 1A and 1B shows a plan view and side view of one transparent capillary flow device in which the method of the invention can be carried out.

One device particularly suitable for use in the practice of the present invention is a commercial embodiment of a capillary flow device described in U.S. Pat. No. 4,756,884, the drawings, specification and claims of which are specifically incorporated herein by reference. This device is referred to as the Protime Cartridge, and is manufactured by Biotrack Inc. of Mountain View, Calif. It is a disposable plastic device about the size of a credit card that measures prothrombin time (PT). The PT measurement is made by applying blood (usually a drop obtained by a fingerstick) to an entry port of a capillary track in the cartridge. Blood flows through the capillary track, where it contacts a reagent comprising thromboplastin, which initiates the clotting response. As blood flows down a capillary track, blood flow is detected by measurement of a speckled pattern cast by red blood cells that intercept a laser beam. When blood flow stops as a result of clotting, changes in the speckle pattern caused by flow also stop, thereby signalling that a clot has formed.

While the Protime reagent cartridge was not designed to measure clot lysis, it has been found to be particularly useful in the practice of one of the methods of the present invention for detecting clot lysis. This method comprises allowing a blood sample containing a plasminogen activator to traverse the capillary track. Since blood clotting occurs more rapidly than blood lysis, a clot will form in the same manner as described above. However, it has been discovered that clot lysis will also occur in a reproducible and measurable manner so that capillary flow reinitiates in the capillary track. The time required for capillary flow to resume can be used as a measure of the thrombolytic activity present in the sample.

It will, of course, be obvious that the method of the present invention need not be carried out in the commercial Protime device but can be carried out in any capillary track containing a reagent capable of initiating blood clotting provided that the capillary track is of sufficient length and sufficiently small volume to allow blood to clot in the track before the sample reaches the end of the track while a reserve sample volume remains available for continued capillary flow once clot lysis has occurred.

Numerous capillary flow devices are described in U.S. Pat. No. 4,756,884, which can be used for guidance in preparing the capillary track. Although the present method could be carried out in a simple capillary tube having interior surfaces coated with the appropriate reagents, the tube being dipped into a sample so that capillary flow can occur, most capillary tracks used in the practice of the invention will be prepared in plastic housings in which the interior capillary tracks are prepared by ultrasonic welding (or other means of attaching) two or more plastic pieces together to form interior chambers, since such methods allow greater ease of adding reagents to the interior of the capillary tracks. In such embodiments, the reagents are added to one or more regions of a depression in the surface of one or more of the pieces. When the pieces are attached together, the reagent is present in the capillary track formed by the surface depressions.

In one preferred device, the capillary track comprises an entry port for introduction of sample, one or more capillary units which principally operate to provide a long track for capillary flow or provide for the transfer of blood from one location to another, one or more chamber units to which reagent has been added, and a vent at the end of the capillary track. The capillaries will usually be of a substantially smaller cross-section or diameter in one direction transverse to the direction of flow in comparison to the chambers or reagent units. However, the chambers and reagent units will have at least one diameter transverse to flow of a capillary dimension in order that capillary flow can continue through these portions of the capillary track. Capillaries will usually have diameters in the range of about 0.01 mm to 2 mm, usually about 0.01 to about 1 mm. The chamber units will have a similar dimension in one direction but will be wider in another direction transverse to flow to provide a broad area to which reagent can be applied. In preferred embodiments, where the capillary track is formed by attaching together plastic pieces with incipient chamber and capillary units present as depressions in the surface of the housing prior to attachment, the relatively broad and shallow chambers provide convenient locations for addition of reagent.

The entry port of the capillary track can merely be a capillary unit as described above leading into the track. Such entry ports are sufficient if other means are provided for contacting the entry port with sufficient sample to allow reaction to occur, such as by dipping the entry port into a sample or placing a drop of blood directly over the entry port and carefully handling the device so as to maintain contact between the drop of blood and the entry port. However, it is also possible to provide a chamber-type entry port, in which the entry port itself is shaped and sized to contain a sufficient volume of sample on which to carry out the assay. Chamber-type entry ports are useful for ease of handling, since an object of the assay is to provide sufficient sample at the entry port (referred to as "reserve sample") to allow sample flow to reinitiate after clot lysis. Typical entry port chamber volumes are 10–100 $\mu$l, preferably 15–75 $\mu$l, more preferably 20–50 $\mu$l.

The total volume of the capillary track is sufficiently small in preferred embodiments for the assay to be carried out on a drop-sized sample. Typical blood drops range from about 20 to about 50 $\mu$l. However, the total capillary track volume can be larger than the drop size if clotting occurs before sample reaches the end of the track. Total track volumes are usually about 20–100 $\mu$l (not counting the holding volume of a chamber-type entry port), preferably about 30–75 $\mu$l, more preferably about 30–50 $\mu$l.

Figure 1B:
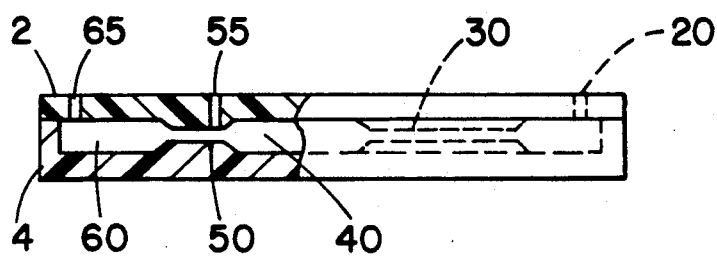

The Protime device, which is typical of devices in which the present method can be carried out, is shown in FIG. 1. FIG. 1 in a plan view showing housing 10, entry port 20, initial capillary unit 30, chamber unit 40 (containing the reagent, not shown), capillary flow unit 50 (in which clotting takes place), and vent 55. Capillary flow unit terminates in alternate entry chamber 60 having alternate entry port 65. Entry port 20 is an aperture in upper plate 2, which, together with lower plate 4, forms housing 10 when plates 2 and 4 are attached. Initial capillary unit 30 and chamber unit 40 are formed from depressions in the lower surface of plate 2. Sections of capillary flow unit 50 are visible (51, 52, 53) when capillary flow unit 50 crosses line A—A.

As sample enters the capillary track through the entry port, it contacts one or more reagents in the capillary track. Techniques for applying sample to capillary tracks and initiating contact between the sample and the reagents are fully described in U.S. Pat. No. 4,756,884. In the present method, at least one reagent will be a reagent capable of initiating blood clotting. Thromboplastin is a reagent of choice.

Other reagents may be present depending on the manner in which the invention is practiced. For example, if the sample is whole blood obtained by venipuncture that contains a calcium-chelating anticoagulant, such as a citrate or ethylenediaminetetraacetic acid salt, calcium ions can be present in the initial portion of the capillary track in an amount sufficient to overcome the anticoagulant effects. However, calcium is not required in the capillary track since it also possible to add calcium to a sample of anticoagulated blood prior to adding the sample to the capillary track.

A plasminogen activator, such as urokinase, strepkinase, or tissue plasminogen activator, can also be present in the capillary track. Such devices would be used in methods where the object of the analysis was to determine whether the patient has a functioning clot lysis system that can be triggered by the plasminogen activator. However, plasminogen activator need not be present when other aspects of a patient's clot lysis system are being measured. For example, the object of the assay may be to determine endogenous thrombolytic capacity of a patient. In such cases no exogenous plasminogen activator is present in the capillary track, nor has an exogenous plasminogen activator been administered to the patient. If the object of the assay is to determine the thrombolytic capacity of a patient to whom exogenous plasminogen activator has been administered, exogenous plasminogen activator in the sample obtained from the patient will be the source of this reagent. Where an in vitro analysis is being carried out to determine which of several plasminogen activators is preferably be used in vivo in a patient, the plasminogen activator can be added to a blood sample after the blood sample is obtained from a patient and before the sample is applied to the capillary track. Particular plasminogen activators and their concentrations can therefore be selected and optimized for a particular patient using a reliable in vitro system.

Figure 2:
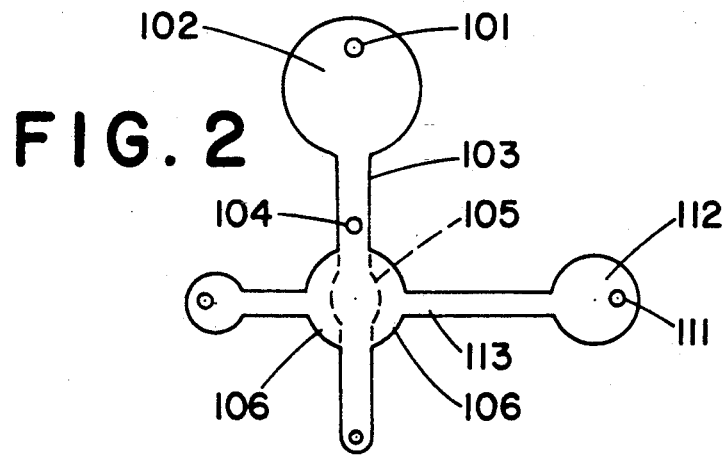
FIG. 2 shows a novel device for use in the practice of the present invention.

The typical thrombosis crisis involves a clot formed in a patient whose blood contains no plasminogen activator, and a decision on treatment options involves evaluation of the efficacy of several available activators and/or dosages on a clot which is significantly blocking the blood vessel. The apparatus of FIG. 2 is particularly useful for this type of evaluation. A sample of blood containing no plasminogen activator is drawn into the apparatus through inlet port 101 and contacted with reagent in first chamber 102 thence flowing through capillary 103 causing the blood to form a clot which will lodge in a permeable or porous tube section 105 disposed within reaction chamber unit 106 said inlet port, first inlet capillary unit, said permeable tube section, first exit capillary unit, and exit port being present in a continuous capillary pathway.

A second sample of blood is drawn through entry port 111 into entry chamber 112 where it is contacted with the lytic drug to be tested if it does not already contain said lytic drug and the second blood sample is caused to flow through capillary 113 to reaction chamber 106 where free flow of the blood sample is partially restricted by the clot within porous tube section 105. The subsequent time to free flow of sample 1 and sample 2 should be substantially the same, and provides a measure of the efficacy of the particular drug and/or dosage level.

FIG. 2a illustrates an alternative embodiment of the device of FIG. 2 showing a sealable vent 11.

Time required for clot lysis can readily be determined using the "speckle pattern" detector system described in U.S. Pat. No. 4,756,884. In this system, flow is detected by a change in light patterns produced by flow of sample between a laser and a light detector, the size and shape of the laser beam being selected so that a speckle pattern results from interaction of red blood cells with the light beam. The size of the light beam is approximately the size of a red blood cell in order for this speckled pattern to be seen. As blood flows through the laser beam, a varying signal is present at the detector. When flow stops, a constant signal is seen. Changing from variation to a constant signal provides the initial signal to indicate that a clot has formed. It is useful, but not necessary, to carry out this measurement at a point in the capillary track before the sample contacts the clotting reagent to avoid interference caused by the clotting process.

In the Protime test (measurement of prothrombin time), measurement ends after clotting is detected. In the present assay, monitoring of the sample continues until flow is reinitiated when clot lysis occurs. When the laser system described above is used, initiation of flow after clotting will be signaled by a change in voltage at the detector from the constant voltage present during stopped flow to a varying voltage as a result of the speckle pattern reappearing when capillary flow resumes.

However, it is not necessary to use the laser system described here to measure flow. For example, initiation of flow can be determined by simple observation, optionally with a low-powered microscope or other magnifying device. Numerous techniques for observing changes in flow rates are described in U.S. Pat. No. 4,756,884.

It will be recognized that the amounts of reagents used in the assay will vary with the particulars of the assay and the specific device used in the assay. Further, since some reagents (e.g., thromboplastin and tissue plasminogen activator) are components of biological origin, their activities will vary from batch to batch. Specific amounts of reagents must therefore be selected by the user (or by a manufacturer of a kit for use in practicing the assay). Such selection is well within the skill of those skilled in the art to which the invention pertains using the guidance provided in this specification. For example, if a particular amount of thromboplastin is tried initially results in clotting so far along the capillary track that no reserve sample remains to initiate flow, the amount of thromboplastin can be adjusted upward or a larger sample can be used. If clot lysis is too slow (about 30 minutes or less is satisfactory, preferably 20 minutes or less, more preferably 10 minutes or less), the amount of thromboplastin can be decreased or the amount of plasminogen activator increased (in assays where exogenous plasminogen activator is used). Similar adjustments can be made empirically to determine suitable amounts of reagents for other circumstance by keeping in mind the object of the adjustments; i.e., (1) to provide a capillary track containing a reagent capable of initiating blood clotting and being of sufficient length and sufficiently small volume to allow blood to clot before the sample reaches the end of the track, and (2) to measure the time required for flow to reinitiate after clotting has stopped flow, flow resumption being caused by either endogenous or exogenous plasminogen activator present in the sample.

The following examples are offered by way of illustration and not by way of limitation.

EXAMPLES

Experiments were carried out to assess the capabilities of the present invention using the Biotrack Protime cartridge described in U.S. Pat. No. 4,756,884, and U.S. Design patent application Ser. No. 915,329, filed Oct. 3, 1986 (now allowed). Citrate anticoagulated venous whole blood was obtained by standard techniques. The anticoagulated blood was mixed with plasminogen activator at the concentrations indicated in the tables below and then immediately recalcified with 0.02M calcium chloride before a drop of the activated sample was transferred to the Biotrack Protein cartridge. This cartridge contains rabbit brain thromboplastin as the reagent capable of initiating blood clotting.

Subsequent events were viewed by light microscopy at several points along the capillary channel. After the sample ceased moving due to thromboplastin-induced coagulation, the red cells were evenly dispersed throughout the reagent area and capillary track. Within several minutes, the red cells begin to form ill-defined, vaguely discernible aggregates of 10-50 cells. The aggregates remained stationary for several minutes, until small channels of reflow appeared with aggregates varying between 2 and 10 red blood cells in diameter. These areas of lysis became increasingly active in the capillary track prior to the reagent chamber (which contained the thromboplastin). Activity progressed to rapid flow throughout the whole capillary. At this point, the aggregates of red blood cells begin breaking free and were swept into the flow of the blood. The timing of the lysis events was a function of the concentration of plasminogen activator added to the blood. Data was obtained for four patients and two plasminogen activators, urokinase and tissue plasminogen activator (tPA). Results are shown in Table 1 and 2 below.

TABLE 1

| tPA Lysis Times (min.) TISSUE PLASMINOGEN ACTIVATOR CONCENTRATION ($\mu$g/ml) | | | | | |
|---|---|---|---|---|---|
| 0.29 | 0.59 | 0.86 | 1.14 | 1.71 | 2.85 |

| | 0.29 | 0.59 | 0.86 | 1.14 | 1.71 | 2.85 |
|---|---|---|---|---|---|---|
| Patient 1 | 16.0 | 11.0 | 10.5 | 8.8 | 8.5 | 7.5 |
| Patient 2 | 35.0 | 23.5 | 16.0 | 11.7 | 9.8 | 7.4 |

TABLE 2

| Urokinase Lysis Times (min.) UROKINASE CONCENTRATION (IU/ml) | | | | |
|---|---|---|---|---|
| | 208 | 417 | 700 | 833 |
| Patient 1 | 10.5 | 8.9 | | 7.0 |
| Patient 2 | | | 6.8 | |
| Patient 3 | | | 4.4 | |
| Patient 4 | | | 2.3 | |

A direct relationship between amount of added plasminogen activator and time required for flow to reinitiate was found (i.e., increasing concentrations of activator reduced the time required for flow to resume).

Figure 3:
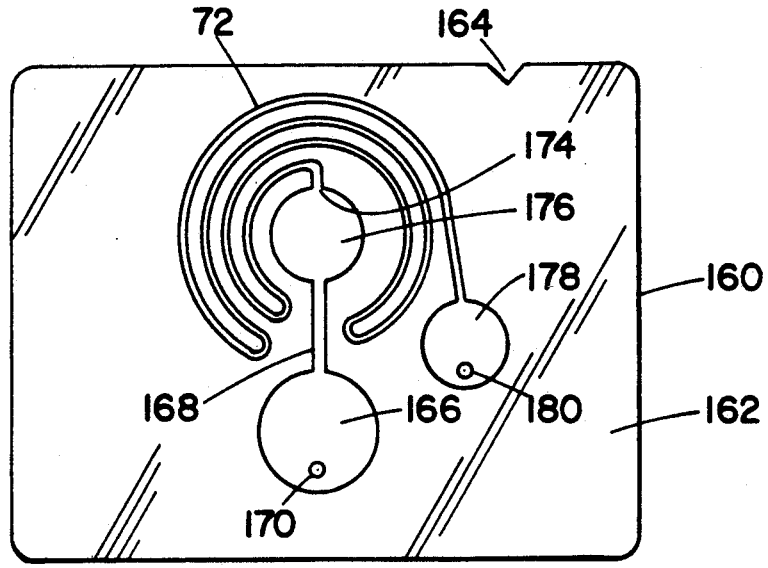
FIG. 3 shows an alternative configuration of the device of FIG. 1.

FIG. 3 corresponds to FIG. 5 of U.S. Pat. No. 4,756,884 and is substantially the same as FIG. 1, except that the capillary tubes are substantially elongated and have a different geometry to facilitate ease of fabrication and optimum compactness. The device of FIG. 3 is the particularly preferred device of the present invention.

As shown in FIG. 3, the embodiment 160 provides a serpentine path. The device has a housing 162 which is a rectangular plastic block shaped to fit into a reading apparatus (not shown). The block is indexed at site 164 for alignment to the apparatus. The receiving chamber 166 has a volume about one and one-half times the volume of the reaction chamber. The two chambers are connected by the first capillary channel 168. Inlet port 170 provides for introduction of the assay sample by syringe, eyedropper, or other convenient means. A serpentine capillary path 172 connects to outlet 174 of reaction chamber 176. The serpentine channel 172 terminates in reservoir chamber 178 which has outlet port 180.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An analytical device for measuring clot lysis time of blood comprising:

a housing containing a chamber including an inlet port and, a permeable tube section constructed so as to contain a blood clot and positioned within a reaction chamber, a first exit port, a first inlet capillary unit for independently pumping blood from said first inlet portion to said permeable tube section, and a first exit capillary unit positioned between and operatively connected to said reaction chamber unit and said first exit port for independently pumping blood from said reaction chamber unit to said first exit port; wherein said inlet port, first inlet capillary unit, said permeable tube section, first exit capillary unit, and exit port are present in a continuous first capillary pathway and said first pathway containing a reagent to affect blood clotting;

said housing further containing a second chamber including a second inlet port connected by second capillary means in fluid communication with said reaction chamber, a second exit capillary means connecting said reaction chamber and a second exit port in a second continuous capillary pathway whereby a second blood supply may be drawn through said inlet port to said reaction chamber into contact with a slot contained in said permeable tube section, and thence to said outlet port.

2. The device of claim 1 wherein said device comprises at least two chamber units in each said pathway.

3. The device of claim 1 further comprising a sealable vent in said first capillary pathway proximal to a juncture between a chamber unit and a capillary unit.

4. The device of claim 1, wherein said reagent is thromboplastin.

5. The device of claim 1 wherein said housing comprises a substantially hydrophobic material having at least a portion of the walls of said capillary pathway treated to provide hydrophilicity.

6. The device of claim 1, said device being fabricated from at least two sheets of substantially hydrophobic plastic, at least one of which is molded to provide depressions for production of said capillary and chamber units, said depressions being treated to provide hydrophilicity, wherein at least one sheet has means defining an orifice forming each said inlet port or exit port, said capillary and chamber units being formed by the joining of said sheets to form said housing.

7. The device of claim 5 wherein said material is a plastic.

8. The device of claim 6 wherein said reagent comprises thromboplastin in said chamber unit.

* * * * *